United States Patent [19]

Sharp et al.

[11] Patent Number: 4,487,829

[45] Date of Patent: Dec. 11, 1984

[54] PRODUCTION AND USE OF MONOCLONAL ANTIBODIES AGAINST ADENOVIRUSES

[75] Inventors: Phillip A. Sharp, Newton; Constance L. Cepko, Allston; Paul Changelian, Brookline, all of Mass.

[73] Assignee: Massachusetts Institute of Technology, Cambridge, Mass.

[21] Appl. No.: 361,017

[22] Filed: Mar. 23, 1982

[51] Int. Cl.³ .................... G01N 33/54; C12P 21/00; C12N 5/00; A61K 39/42
[52] U.S. Cl. .......................................... 435/7; 435/68; 435/240; 435/172.2; 435/948; 436/548; 424/86; 935/110; 935/104; 935/92; 260/112 R
[58] Field of Search ............... 435/7, 68, 172, 240, 435/241, 948, 235, 236, 239; 424/85, 86, 88, 89; 260/112 R; 436/548

[56] References Cited

U.S. PATENT DOCUMENTS 4,053,284 10/1977 Posch ............................. 436/820
4,196,265 4/1980 Koprowski et al. ............ 435/240

OTHER PUBLICATIONS

Russel et al., "Monoclonal Antibodies Against Adenovirus Type 5: Preparation and Preliminary Characterization" Journal of General Virology 56 (10–1980) pp. 393–408.
Philipson et al., "Reproduction of Adenoviruses" Comprehensive Virology, vol. 3, (1974), pp. 143–227.
David et al., "The Hybridoma—An Immunochemical Laser" Clinical Chemistry 27 (9) (1981), pp. 1580–1585.
Noonan et al., "Application of Monoclonal Antibodies to Study the Distribution of Cell Surface Proteins: Prospects and Problems" Monoclonal Antibodies in Endocrin Research, Raven Press, (1981), pp. 41–52.
Foy et al., "Adenoviruses" in Viral Infections of Humans, by Evans, Plenum Medical Book Co., NY, (1976), pp. 53–55.
Cepko et al., "Immunoprecipitation with Two Dimensional Pools as a Hybridoma Screening Technique: Production and Characterization of . . ." Virology 110 (1981), pp. 385–401.
Herzenberg et al., "Cell Hybrids of Myelomas with Antibody Forming Cells and T-Lymphomas with T Cells" Handbook of Experimental Immunology, Blackwell Publ., pp. 25.1–25.7.
Kohler et al., "Continuous Cultures of Fused Cells Secreting Antibody of Predefined Specificity" Nature 256 (8–1975), pp. 295–297.
Galfry et al., "Antibodies to Major Histocompatibility Antigens Produced by Hybrid Cell Lines" Nature vol. 266 (1977) pp. 550–552.
Nowinski et al., "Mapping of Viral Proteins with Monoclonal Antibodies" Monoclonal Antibodies: Hybridoma: A New Dimension in Biological Analysis Kennet et al., ed. Plenum Press NY (1980) part 5, pp. 295–359.
Cuello et al., "Detection of Substance P in the Central Nervous System by a Monoclonal Antibody" Proceedings of the National Academy of Sciences, 78(7) (1979), pp. 3532–3536.

Primary Examiner—Thomas G. Wiseman
Assistant Examiner—John E. Tarcza
Attorney, Agent, or Firm—Arthur A. Smith, Jr.; Thomas J. Engellenner

[57] ABSTRACT

Monoclonal antibodies, and a cell line characterized by its production of such monoclonal antibodies, demonstrating specific reactivity to an antigenic determinant possessed by a plurality of types of adenoviruses, a method of isolating such cell lines, and the use of such antibodies for diagnostic and therapeutic purposes as well as for identifying chemical compounds with similar properties, are disclosed.

15 Claims, No Drawings

PRODUCTION AND USE OF MONOCLONAL ANTIBODIES AGAINST ADENOVIRUSES

The government has rights in this invention pursuant to National Institute of Health Grant No. NIH-S-PO1-CA26717-02.

TECHNICAL FIELD

This invention relates to monoclonal antibodies and, in particular, to monoclonal cell lines secreting antibodies to adenoviruses.

BACKGROUND OF THE INVENTION

The cell lines of this invention have been deposited in the regular course of business in the ATCC. The coding numbers are HB8117. The publication describing the invention can be found in Cepko, C. L., Changelian, P. S., and Sharp, P. A.: "Immunoprecipitation with Two-Dimensional Pools as a Hybridoma Screening Technique: Production and Characterization of Monoclonal Antibodies Against Adenovirus 2 Proteins", *Virology*, Vol. 110, pp. 385–401 (1981) herein incorporated by reference.

Adenoviruses are nonenveloped viruses 65–80 nM in diameter. The virion is an icosahedron composed of 252 capsomers. These capsomers are primarily composed of a trimer of the hexon protein (Hx) which has been designated polypeptide II. The virion also contains about 14 other virus encoded polypeptides as well as a single duplex DNA genome. This genome has a molecular weight of approximately $25 \times 10^6$ daltons.

The hexon capasomer is the major structural component of the virion. It has a molecular weight of about 360,000 daltons and is composed of three identical polypeptide chains (abbreviated by size classification as "II"). The DNA region encoding polypeptide II has been sequenced by others for human adenovirus 2, thus mapping the viral protein between coordinates 52.5 and 62.5 map units (M.U.) (r strand) and determining its amino acid sequence.

Low-angle X-ray diffraction studies of purified hexon trimers have shown the capsomer to have a pyramid-type structure with a hole down the middle. The small end of the pyramid is exposed to the exterior of the virion, the large end apparently embedded in the interior.

Adenoviruses have been classified into 80 different types by a combination of features, but primarily morphology and serology. There are 31 human, 23 simian, 10 bovine, 1 ovine, 2 canine, 2 murine, 1 frog, 4 porcine, 8 avian, and 1 opossum types known. All of these types (except avian and amphibian) are believed to contain one group specific antigenic determinant in the hexon capsomer. For example, antiserum raised against hexon capsomers of one type will react with this determinant on other types. This group-specific antigen determinant is not exposed on the surface of the virion and is destroyed in disruption of the trimer conformation of the Hx.

Antigenic determinants that are type or subgroup specific are exposed on the surface of the virion. Some of these determinants are associated with Hx, others are features of other virion components. Neutralizing antibodies are primarily type-specific but also have some subgroup specificity. Subgroups of adenovirus are also based on similarities in DNA sequence and biology of the viruses.

The first strain of adenovirus was isolated in 1953 from infected adenoids of man. Adenovirus infections of humans can be associated with respiratory disease, conjunctivitis, myocarditis and enteritis. Adenovirus infections are common and can, in rare cases, be fatal (for example, non-bacterial pneumonia in infants). Adenovirus infections can be diagnosed serologically and by isolation of the offending virus from respiratory and ocular secretions, urine, and feces. Serology typically involves either complement fixation, immunofluorescence, radioimmunoassay or another antibody-antigen binding assays with group-specific antiserum. Type-specific recognition can be determined by neutralization or inhibition of hemagglutination assays with type-specific antiserum.

We are not aware of anyone who has isolated monoclonal antibodies which are group specific to an antigenic determinant of adenoviruses. There exists a need for such antibodies in relatively pure form for research. Moreover, the usefulness of such antibodies in diagnostic kits and screening techniques should be apparent as a substitute for the present type specific immunological tests for detecting the presence of adenoviruses.

SUMMARY OF THE INVENTION

We have discovered and isolated a hybridoma cell line that secretes monoclonal antibody to an adenovirus group-specific antigenic determinant. This monoclonal antibody will provide a high titer, reproducible, biological reagent for diagnoses of adenovirus infections, both human and animal. The monoclonal antibody recognizes an antigenic determinant on Hx which is common among human, simian, bovine, swine, canine, and probably all adenoviruses that infect mammalian hosts. Our antibodies may also find use in analyzing other chemical substances for affinity to the group specific determinant.

DETAILED DESCRIPTION OF THE PREFERRED EMBODIMENTS

A hybridoma secreting monoclonal antibody to an adenovirus group specific antigenic determinant was isolated by fusion of lymphocytes from spleen cells of mice immunized with soluble infected cell extracts. These spleen cells were fused to either myeloma clone P3-x63-Ag8 or SP2/0. Hybridoma colonies were screened for production of antibodies specific for reaction with hexon trimer and not denatured or monomer hexon. Hybridomas in the latter group were tested for binding to different types of adenoviruses. The spectrum of reactivity suggested that certain hybridomas secreted antibodies to an adenovirus group specific antigenic determinant.

Adenovirus 2 (Ad2) was propagated and titered in HeLa cells. Virus and cell fractions were prepared by banding of extracts in CsCl density gradients.

Balb/c mice, 8–10 weeks old, were primed intraperitoneally ("ip") and then immunized (ip) three times over a three month period. Mice were immunized with two different types of antigen preparations, native virions irradiated with UV (200 ug each injection) or extracts of infected cells 44 hours postinfection ("hpi."). In the latter case, infected cells were lysed in 0.01M Tris pH 7.9 and homogenized with an equal volume of freon. After centrifugation, the upper aqueous phase containing both virions and soluble virus components was fractionated by further centrifugation on top of a CsCl step gradient to remove virus. The aqueous phase was dialyzed into 20 mM Tris, pH 8.0, 1 mM $MgCl_2$ and 5% glycerol. Infected cell proteins from $2 \times 10^7$ cells were used in each injection.

Four mice were immunized with each type of antigen preparation. Two of the four mice were immunized with Freund's adjuvant, complete Freund's for the primary injection and incomplete Freund's for the boosts.

Spleen cells from mice immunized with irradiated virions were fused to P3-x63-Ag8 myeloma cells (Kohler and Milstein, 1976). Spleen cells from mice immunized with soluble virus proteins were fused with SP2/0. In both cases, fusion was mediated by polyethylene gylcol. Hybrids were plated in HAT media in microtiter wells two days after fusion. The cells were seeded at $3 \times 10^4$ or $10^5$ myeloma cells/well. 100 ul of HAT media was added to each microtiter well five days after plating. Culture media was screened for monoclonal activity 12–15 days after plating. Positive wells were split ¼ or 1/10 into 24-well macrotiter dishes. Subsequently, cells were either cloned in soft agar or by limiting dilution. Each clone was then re-cloned by one of these procedures.

A radioimmune binding assay was used as a primary screening technique for hybrid culture supernatants. Antigens for this assay were either purified virions heated for 10 min. at 56° (to disrupt structure) or infected cell extracts prepared by freeze-thawing and centrifugation. The latter soluble extract was also heated before binding to polyvinyl chloride microtiter plate. 20 ul of culture media was tested for specific binding and was detected by binding of either $^{125}$I-labeled rabbit anti-mouse IgG (RAMIGG) or $^{125}$I labeled Staphylococcus aureus (Staph A) Protein A purchased from Pharmacia.

Immunoprecipitations were performed using the Staph A method. In some cases, goat α-mouse serum was included. Staph A was used as a stock 10% suspension, rehydrated from lyophilized material purchased from Enzyme Center, Inc., Boston, Mass. For culture supernatants, 50–200 ul of Staph A suspension was added.

When immunoprecipitation was used as a primary screening method, pools of culture supernatants were made. Each 96-well microtiter dish was divided into 20 pools. Pools A–H were made by combining 50 ul of supernatant from each of the wells in a given row. Similarly, pools 1–12 were made by combining supernatants from each well in a given column. The precise identification of a positive well could then be made, as it contributed to two pools corresponding to its location on the microtiter dish. The pools of supernatants were incubated with antigen overnight (8–10 hr). An incubation with 7 ul of goat α-mouse serum and 200 ul 10% Staph A followed.

$^{35}$S-methionine labeled cell lysates were prepared by exposing cell monolayers to 25–30 uCi/ml of $^{35}$S-methionine (Amersham, 700–1100 Ci/mmol) in DME-methionine. Cells were typically labeled 16–17 hpi and harvested immediately. For labeling of purified trimers, cells were labeled 24–36 hpi. Monomeric hexon was prepared by in vitro translation of mRNA extracted from late Ad2 infected cells (32 hpi).

Indirect immunofluorescent staining of Ad2-infected HeLa cells was performed. Infected cells were harvested for staining at 29 hpi. The fluorescent rabbit α-mouse antibody was obtained from Miles-Yeda.

Hybridomas created by fusion of spleen cells from mice immunized by soluble antigens (from infected cell extracts made free of virion particles) were screened by immunoprecipitation of pools formed by combining culture supernatants in the two dimensional fashion described above. The pooled supernatants were mixed with $^{35}$S-methionine labeled Ad2 infected cell extracts, immunoprecipitated, and resolved by polyacrylamide gel electrophoresis. Wells contributing to immunoprecipitation of the 120,000 dalton hexon protein were individually screened by immunoprecipitation. Cells from wells positive for specific immunoprecipitation of only hexon (trimers of polypeptide II) were further cloned by limiting dilution. During subcloning, wells positive for secretion of viral specific antibodies were detected by screening with radioimmunoassays. All hybridomas were subcloned twice and remained stable upon further culturing.

Hybridomas specific for immunoprecipitation of hexon (trimers of polypeptide II) from infected cell extracts were selected for further characterization as to their reactivity with group specific antigenic determinants. Hybridoma 2-Hx-2 was one of this group. $^{35}$S-methionine labeled hexon (trimers of polypeptide II) was prepared from infected HeLa extracts by DEAE chromatography. The trimer nature of this preparation was tested by sedimentation in sucrose gradient where all the $^{35}$S-label sedimented as expected at 12S. Our preferred hybridomas secreted monoclonal antibodies that quantitatively immunoprecipitated this 12S $^{35}$S-labeled hexon. These hybridomas were also positive for immunoprecipitation of hexon from disrupted virions. They were negative for immunoprecipitation of $^{35}$S-methionine labeled monomers of hexon prepared by in vitro translation of mRNAs from late infected cells or denatured $^{35}$S-methionine labeled hexon polypeptides prepared by boiling purified hexon trimers in 1% SDS, 0.5% β-mercaptoethanol for 2 min. Supernatants from these hybridomas were also negative for immunoprecipitation of intact $^{35}$S-methionine labeled virions. The spectrum of reactivity of our preferred hybridomas from this collection suggested that they recognized a determinant on hexon which has some of the expected properties of a group specific determinant.

A number of other properties of the monoclonal antibody secreted by hybridoma 2-Hx-2 were examined and are listed in Table I. These properties were the same if antibody was tested from culture media or ascites fluid. (Ascites fluids were prepared by injection of 0.5 ml of pristane ip 2–4 weeks before injection of $1-2 \times 10^6$ tumor cells. Fluids were collected typically three weeks later, centrifuged for 3 hr. at 35,000 rpm and supernatants stored at −70°).

TABLE I

Properties of Monoclonal Antibody 2-Hx-2

1. Class: IgG (Staph A binding positive)
2. Adenovirus 2 neutralization-negative
3. Ouchterlony precipitation of Ad2 infected cell extracts - negative
4. Nuclei of Ad2 infected cells stain brightly positive by indirect immunofluorescence
5. Immunoprecipitation positive for hexon of human Ad2 and Ad5
6. Positive for immunofluorescent staining of nuclei of cells infected by bovine (BAV-1 and BAV-7), canine (CAV-1 and CAV-2), swine (SAV), simian (SA7) and human subgroups A (31), B (21,11,3,7), C (1,2,5) D (19), E (4) adenoviruses
7. Positive for detection of antigenic determinants by Elisa assay for adenovirus infections of human cells
8. Negative for reactivity to determinants in avian adenovirus infected cells as assayed by immunofluorescence The broad spectrum of reactivity of this monoclonal antibody with different adenovirus types, and its unique binding to hexon (trimers) suggest that it recognizes a group specific determinant. The antibody is of high avidity, and binds Staph A. The hybridoma (2-Hx-2) secreting this antibody yields high titer ascites fluid (dilutions of 1/10,000 are possible for immunofluorescence). This hybridoma and the antibody it secretes will be valuable reagents for use in diagnostic tests for detection of human or animal adenovirus components. Fluids or tissue from animals can be screened by either radioimmunoassay, immunofluorescence, complement fixation, immunoprecipitation or any reaction that depends on antibody recognition of antigen for detection of adenovirus infections. Given the group specific nature of the antibody binding, all animal adenovirus types should be detected with this single reagent.

We claim:

1. A monoclonal antibody demonstrating specific reactivity to an antigenic determinant possessed by a plurality of types of adenoviruses, the antibody characterized further by its reactivity with hexon trimers derived from adenoviruses and its lack of reactivity in immunoprecipitation reactions with intact adenovirus virions, denatured hexon polypeptides and monomeric hexon polypeptides.

2. The monoclonal antibody according to claim 1 and further characterized by its positive immunoprecipitation of hexon trimers derived from capsomers of human Ad2 and human Ad5 adenoviruses.

3. A monoclonal antibody demonstrating:
   a. positive reaction to hexon trimer;
   b. lack of reactivity with denatured or monomeric hexon;
   c. inability to immunoprecipitate intact adenovirus virions;
   d. lack of adenovirus neutralizing activity;
   e. nuclear immunofluorescence in cells where adenoviruses are present;
   f. reactivity with human subgroups A-E, simian, bovine, canine and swine adenoviruses; and
   g. lack of reactivity with avian adenovirus.

4. A monoclonal antibody having the following characteristics:
   a. being of IgG class of immunoglobulin molecules;
   b. demonstrating negative neutralization for human adenovirus type 2;
   c. demonstrating negative precipitation by the Ouchterlony technique for extracts from cells infected with human adenovirus type 2;
   d. staining nuclei of adenovirus type 2 infected cells positive by indirect immunofluorescence techniques; and
   e. demonstrating specific reactivity to an antigenic determinant possessed by a plurality of types of adenoviruses.

5. In process for detecting the presence of adenoviruses comprising contacting sample with antibody and measuring the reaction, the improvement comprises using monoclonal antibodies demonstrating reactivity to an antigenic determinant possessed by a plurality of types of adenoviruses and characterized further by its reactivity with hexon trimers derived from adenoviruses and its lack of reactivity in immunoprecipitation reactions with intact adenovirus virions, denatured hexon polypeptides and monomeric hexon polypeptides.

6. The process of claim 5 wherein the step of testing the sample further comprises testing by complement fixation.

7. The process of claim 5 wherein the step of testing the sample further comprises testing by immunofluorescence.

8. The process of claim 5 wherein the step of testing the sample further comprises testing by radioimmunoassay.

9. The process of claim 5 wherein the step of testing the sample further comprises testing by Elisa assay.

10. The process of claim 5 wherein the step of testing the sample further comprises testing by immunoprecipitation.

11. The process of claim 5 wherein the step of testing the sample further comprises testing by immunoelectron microscopy.

12. A hybridoma cell line characterized by its production of monoclonal antibodies demonstrating specific reactivity to an antigenic determinant possessed by a plurality of types of adenoviruses, the cell line further characterized by its production of monoclonal antibodies demonstrating a lack of reactivity in immunoprecipitation reactions with intact adenoviruses, denatured hexon polypeptides, and monomeric hexon polypeptides.

13. An antibody-producing cell line having the identifying characteristics of ATCC HB8117.

14. A method of isolation of hybricomas secreting monoclonal antibodies to adenovirus group specific antigenic determinants comprising screening a group of hybridomas for antigen-antibody reactions to hexon trimers, testing the hybridomas, which demonstrate positive reactions with the hexon trimers derived from adenoviruses, for cross reactivity with various adenovirus types lack reactivity in immunoprecipitation reactions with intact adenovirus virions, denatured hexon polypeptides and monomeric hexon polypeptides and separating the hybridomas that demonstrate cross-reactivity in addition to positive reactions with the hexon trimers.

15. A method of analyzing chemical compounds for affinity to a group specific determinant of adenoviruses by measuring their competition with monoclonal antibodies which demonstrate specific reactivity with hexon trimers derived from adenoviruses and a lack of reactivity in immunoprecipitation reactions with intact adenoviruses, denatured hexon polypeptides, and monomeric hexon polypeptides.

* * * * *